United States Patent [19]

Hatch, III

[11] 4,254,279

[45] Mar. 3, 1981

[54] ESTER RESOLUTION PROCESS

[75] Inventor: Charles E. Hatch, III, Pennington, N.J.

[73] Assignee: FMC Corporation, Philadelphia, Pa.

[21] Appl. No.: 78,412

[22] Filed: Sep. 24, 1979

Related U.S. Application Data

[63] Continuation-in-part of Ser. No. 24,149, Mar. 26, 1979, abandoned.

[51] Int. Cl.$^3$ ............................................. C07C 69/72
[52] U.S. Cl. .................................... 560/178; 560/35; 560/38
[58] Field of Search ........................... 560/35, 178, 38

[56] References Cited

U.S. PATENT DOCUMENTS

| | | | |
|---|---|---|---|
| 2,577,900 | 12/1951 | Lisk et al. | 560/35 |
| 4,024,163 | 5/1977 | Elliott et al. | 260/501.1 |
| 4,027,037 | 5/1977 | Siegle et al. | 560/39 |

OTHER PUBLICATIONS

Adams et al., J.A.C.S., 88, 162, 1966.
Potapor et al., Chem. Absts., 3352(g) vol. 57, 1962.
Coward et al., J.A.C.S., 91, 5329, 1969.
G. Stork et al., J.A.C.S., 85, 207 (1963).

*Primary Examiner*—Natalie Trousof
*Assistant Examiner*—G. T. Breitenstein
*Attorney, Agent, or Firm*—Richard L. Hansen; Henry R. Ertelt

[57] ABSTRACT

Optically active 1-Trichloromethyl-3-methyl-2-butenyl acetoacetate is prepared by resolving the racemic ester via a crystalline enamine derivative.

2 Claims, No Drawings

ESTER RESOLUTION PROCESS

This is a continuation-in-part of application Ser. No. 024,149, filed Mar. 26, 1979, now abandoned.

This invention relates to novel processes and intermediates for the resolution of racemic esters.

U.S. Pat. No. 4,024,163 discloses a process for making insecticidal esters from 3-(2,2-dihalovinyl)-2,2-dimethylcyclopropanecarboxylic acids, for example, from optically active (1S,3S)- and (1R,3R)-3-(2,2-dihalovinyl)-2,2-dimethylcyclopropanecarboxylic acids. The latter acids may be prepared from (S)- and (R)-1-trihalomethyl-3-methyl-2-butenyl acetoacetates, respectively, as disclosed in application Ser. No. 950,903, filed Oct. 12, 1978, now abandoned. The disclosures of these references are incorporated herein.

It is one object of this invention to provide a method for preparing (S)- or (R)-1-trihalomethyl-3-methyl-2-butenyl acetoacetates by resolving racemic 1-trihalomethyl-3-methyl-2-butenyl acetoacetates. It is another object of this invention to provide novel intermediate compounds, enamine-esters, for use in the resolution.

Beta-keto esters, such as 1-trihalomethyl-3-methyl-2-butenyl acetoacetates, contain two functional groups, ketone and ester, which could be reactive sites for derivatization and ultimate separation of the two enantiomers. It is known in the art to resolve racemic esters by hydrolysis to an acid, reaction of the acid with an optically active base to produce a salt, separation of the salt diasteriomers, and reesterification to generate the ester. It is also known in the art to resolve racemic ketones by employing optically active reagents and producing diasteriomeric hydrazides, amine bisulfites, oximes, iminium salts, and so forth. The methods of the prior art suffer from various disadvantages; for example, the derivative may not be a solid, making it difficult to separate the diasteriomers, or the derivative may be difficult to cleave.

The resolution of a beta-keto ester presents further complications, tautomeric enolization of α-hydrogen atoms making possible the concurrent formation of several diasteriomeric pairs from a single derivatizing agent, compounding the separation problems. The prior art [Chem. Abstr., 57, 3352 g (1962)] discloses the reaction of the beta-keto ester, ethyl acetoacetate, with (−)-α-phenylethylamine to produce an unstable solid ketimine, which tautomerizes to a liquid enamine at room temperature. U.S. Pat. No. 4,027,037 discloses a large number of enamine derivatives of acetoacetic esters. With the exception of one low melting solid, all those enamines are liquids.

By contrast, it has now been found that a racemic 1-trihalomethyl-3-methyl-2-butenyl acetoacetate can be resolved via a high melting solid enamine derivative, whose structural formula appears below, the derivative being a pair of solid diasteriomers, which are separated by fractional crystallization, one of the diasteriomers yielding the desired (R)-1-trihalomethyl-3-methyl-2-butenyl acetoacetate by mild selective hydrolysis of the enamine, the other diasteriomer similarly yielding the (S)-acetoacetate.

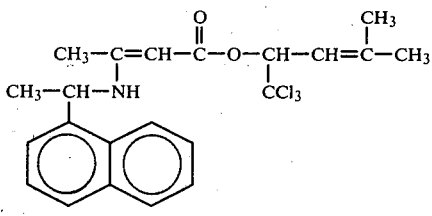

According to a method of this invention, for example, racemic 1-trichloromethyl-3-methyl-2-butenyl acetoacetate, which may be prepared by treating 1,1,1-trichloro-4-methyl-3-penten-2-ol (see German Offen. No. 2,542,377 for synthesis) with diketene, is condensed with an approximately equimolar amount of either (R)- or (S)-1-(1-naphthyl)ethylamine in an aprotic organic solvent to produce an enamine, whose structural formula appears above, a mixture of the diasteriomers, (R)-3-methyl-1-trichloromethylbut-2-en-1-yl (R)-3-[N-(1-(1-naphthyl)ethyl)amino]but-2-enoate and (S)-3-methyl-1-trichloromethylbut-2-en-1-yl (R)-3-[N-(1-(1-naphthyl)ethyl)amino]but-2-enoate when (R)-1-(1-naphthyl)ethylamine is employed, or (R)-3-methyl-1-trichloromethylbut-2-en-1-yl (S)-3-[N-(1-(1-naphthyl)ethyl)amino]but-2-enoate and (S)-3-methyl-1-trichloromethylbut-2-en-1-yl (S)-3-[N-(1-(1-naphthyl)ethyl)amino]but-2-enoate when (S)-1-(1-naphthyl)ethylamine is used, which mixture may optionally be recovered as a solid from the solvent.

An acid catalyst is not strictly required in the condensation, but it is desirable to use a catalytic amount of strong acid, protonic mineral acid or sulfonic acid. Examples of such acids are HCl, HBr, $H_2SO_4$, $HNO_3$, $H_3PO_4$, and p-toluenesulfonic acid. In the context of this condensation, a catalytic amount of acid means equal to or less than 5 mole percent of the reactants, preferably 1–4 mole percent. A number of aprotic organic solvents may be employed in the condensation; for example, aromatic hydrocarbons, such as benzene, toluene, and xylene; aliphatic and cycloaliphatic hydrocarbons, such as hexane, heptane, octane, and cyclohexane; ethers, such as tetrahydrofuran and dioxane; amides, such as dimethylformamide; as well as dimethylsulfoxide and acetonitrile, for example. These solvents may be used singly or in combination with each other. Among these solvents, toluene and acetonitrile are especially desirable, and acetonitrile is preferred. Recovery of the mixture of diasteriomers from the solvent is effected by methods known in the art, for example, evaporation of the solvent, cooling or seeding to cause crystallization, followed by filtration, and so forth.

The mixture of two diasteriomers may be separated into the two optically active components by crystallization under suitable conditions. For example, (R)-3-methyl-1-trichloromethylbut-2-en-1-yl (S)-3-[N-(1-(1-naphthyl)ethyl)amino]but-2-enoate substantially free of (S)-3-methyl-1-trichloromethylbut-2 -en-1-yl (S)-3-[N-(1-(1-naphthyl)ethyl)amino]but-2-enoate is prepared by crystallizing or recrystallizing the mixture of these two diasteriomers from acetonitrile and recovering the (R)-3-methyl-1-trichloromethylbut-2-en-1-yl (S)-3-[N-(1-(1-naphthyl)ethyl)amino]but-2-enoate as the first crystalline precipitate. Recrystallization is conveniently carried out by dissolving about 2–4 g of the solid mixture of diasteriomers in about 100 milliliters of solvent at the reflux temperature, then allowing the resulting solution to cool to room temperature (20°–25° C.) The precipitate which deposits from the solution is isolated by methods known in the art. If the other diasteriomer is desired, it may be obtained from the residual solution by conventional methods.

The desired optical isomer of 1-trichloromethyl-3-methyl-2-butenyl acetoacetate may be regenerated from the appropriate diasteriomer by selectively hydrolyzing the enamine function without affecting the ester linkage. For example, (R)-1-trichloromethyl-3-methyl-2-butenyl acetoacetate substantially free of the (S)-optical isomer is prepared by selectively hydrolyzing (R)-3-methyl-1-trichloromethylbut-2-en-1-yl (S)-3-[N-(1-(1-naphthyl)ethyl)amino]but-2-enoate in an aprotic, water-miscible organic solvent with aqueous mineral acid. Aprotic, water-miscible organic solvents which may be employed in the selective hydrolysis include ethers, such as tetrahydrofuran and 1,2-dimethoxyethane, amides, such as dimethylformamide, as well as dimethylsulfoxide and acetonitrile. Mineral acids which may be employed in the cleavage include HCl, HBr, $HNO_3$, $H_3PO_4$, and $H_2SO_4$. Although the precise amount of aqueous mineral acid is not critical, the reaction mixture should be acidic, and it is preferred to employ between about 1 and 20 equivalents of acid, generally between 2 and 10 equivalents, per equivalent of enamine. It is also preferred to add the acid as a dilute aqueous solution, about 0.1 to 4 N, especially about 0.5 N.

The process of this invention will be understood more completely by reference to the following Examples.

EXAMPLE I

Preparation and Recrystallization of 3-Methyl-1-trichloromethylbut-2-en-1-yl 3-[N-(1-(1-naphthyl)ethyl)amino]but-2-enoate A. A mixture of 1-trichloromethyl-3-methyl-2-butenyl acetoacetate (11.5 g, 0.04 mole), (S)-1-(1-naphthyl)ethylamine (7.08 g, 0.04 mole), two drops of concentrated sulfuric acid, and toluene (240 ml) was stirred at room temperature for approximately 18 hours. The reaction mixture was filtered to remove a small amount of amine sulfate salt, then concentrated under reduced pressure. The resultant residue was triturated with 200 ml hexane to give a mixture of (R)-3-methyl-1-trichloromethylbut-2-en-1-yl (S)-3-[N-(1-(1-naphthyl)ethyl)amino]but-2-enoate and (S)-3-methyl-1-trichloromethylbut-2-en-1-yl (S)-3-[N-(1-(1-naphthyl)ethyl)amino]but-2-enoate as a yellowish-white powder; mp, 183°–194° C. This powder was recrystallized from acetonitrile three times to yield (R)-3-methyl-1-trichloromethylbut-2-en-1-yl (S)-3-[N-(1-(1-naphthyl)ethyl)amino]but-2-enoate (1.26 g, 95% optically pure); mp. 209°–210.5° C.

Analysis: Calc. for $C_{22}H_{24}Cl_3NO_2$: C, 59.95; H, 5.49; N, 3.18. Found: C, 59.69; H, 5.27; N, 3.42.

nmr δ ppm (CDCl$_3$): 1.6 (doublet,3H); 1.7 (singlet, 3H); 1.8–2.0 (double singlet, 6H); 4.6 (singlet, 1H); 5.2–5.7 (multiplet, 2H); 6.3 (doublet, 1H); 7.3–8.1 (multiplet, 7H); 9.0 (multiplet, 1H).

B. A mixture of 1-trichloromethyl-3-methyl-2-butenyl acetoacetate (84.1 g, 0.292 mole), (S)-1-(1-naphthyl)ethylamine (50.0 g, 0.292 mole), two drops of concentrated sulfuric acid, and acetonitrile (1680 ml) was stirred for approximately 16 hours at room temperature, then seeded with (R)-3-methyl-1-trichloromethylbut-2-en-1-yl (S)-3-[N-(1-(1-naphthyl)ethyl)amino]but-2-enoate. After an additional 72 hours of stirring, the reaction mixture was filtered to yield (R)-3-methyl-1-trichloromethylbut-2-en-1-yl (S)-3-[N-(1-(1-naphthyl)ethyl)amino]but-2-enoate (32.4 g, 88% optically pure); mp, 193°–198° C. The solid was recrystallized once from 1700 ml of acetonitrile to yield (R)-3-methyl-1-trichloromethylbut-2-en-1-yl (S)-3-[N-(1-(1-naphthyl)ethyl)amino]but-2-enoate (22.3 g, 95% optically pure, 35% yield); mp, 205°–207.5° C.

EXAMPLE II

Preparation of (R)-1-Trichloromethyl-3-methyl-2-butenyl acetoacetate

To a solution of (R)-3-methyl-1-trichloromethylbut-2-en-1-yl (S)-3-[N-(1-(1-naphthyl)ethyl)amino]but-2-enoate (10 g, 0.023 mole) in tetrahydrofuran (200 ml) at room temperature was added, in one portion, 0.5 N aqueous hydrochloric acid (250 ml, 0.125 mole). Upon addition of the acid, a white precipitate formed immediately, then slowly disappeared. The mixture was stirred at room temperature for a total of 62 hours and then extracted three times with 200 ml of hexane, after which the combined organic phases were dried over sodium sulfate and concentrated under reduced pressure. The pale yellow oily residue was distilled to yield (R)-1-trichloromethyl-3-methyl-2-butenyl acetoacetate (5.57 g, 85% yield); bp, 90°–92° C. (0.05 mmHg); $[\alpha]_D^{25} = +13.00°$ (CHCl$_3$).

I claim:

1. A process for resolving 1-trichloromethyl-3-methyl-2-butenyl acetoacetate which comprises
    (i) condensing 1-trichloromethyl-3-methyl-2-butenyl acetoacetate with optically active 1-(1-naphthyl)ethylamine in acetonitrile using a catalytic amount of protonic mineral acid or sulfonic acid,
    (ii) crystallizing or recrystallizing the resultant mixture of enamine diastereomers from acetonitrile, employing 2–4 g of said mixture per 100 ml of acetonitrile, recovering one diastereomer as the first crystalline precipitate and the other in the residual solution, and then
    (iii) hydrolyzing at least one of the recovered diastereomers in a mixture of tetrahydrofuran and aqueous mineral acid selected from HCl, HBr, HNO$_3$, H$_3$PO$_4$, and H$_2$SO$_4$, about 1–20 equivalents of 0.1 to 4 N aqueous acid being employed for each equivalent of diastereomer.

2. A process for preparing (R)-1-trichloromethyl-3-methyl-2-butenyl acetoacetate substantially free of the (S)-optical isomer which comprises
    (i) condensing racemic 1-trichloromethyl-3-methyl-2-butenyl acetoacetate with (S)-1-(1-naphthyl)ethylamine in acetonitrile using a catalytic amount of protonic mineral acid or sulfonic acid,
    (ii) crystallizing or recrystallizing the resultant mixture of (R)-3-methyl-1-trichloromethylbut-2-en-1-yl (S)-3-[N-(1-(1-naphthyl)ethyl)amino]but-2-enoate and (S)-3-methyl-1-trichloromethylbut-2-en-1-yl (S)-3-[N-(1-(1-naphthyl)ethyl)amino]but-2-enoate from acetonitrile, employing 2–4 g of said mixture per 100 ml of acetonitrile, recovering (R)-3-methyl-1-trichloromethylbut-2-en-1-yl (S)-3-[N-(1-(1-naphthyl)ethyl)amino]but-2-enoate as the first crystalline precipitate, and then
    (iii) hydrolyzing the recovered (R)-3-methyl-1-trichloromethylbut-2-en-1-yl (S)-3-[N-(1-(1-naphthyl)ethyl)amino]but-2-enoate in a mixture of tetrahydrofuran and aqueous mineral acid selected from HCl, HBr, HNO$_3$, H$_3$PO$_4$, and H$_2$SO$_4$, about 1–20 equivalents of 0.1 to 4 N aqueous mineral acid being employed for each equivalent of (R)-3-methyl-1-trichloromethylbut-2-en-1-yl (S)-3-[N-(1-(1-naphthyl)ethyl)amino]but-2-enoate.

* * * * *